United States Patent
Lupano et al.

(10) Patent No.: US 9,066,652 B2
(45) Date of Patent: Jun. 30, 2015

(54) METHOD AND MEDICAL DEVICE FOR REDUCING THE EFFECTS OF INTERFERENCE GENERATED BY A RADIO TRANSMISSION FROM THE MEDICAL DEVICE

(75) Inventors: Michele Lupano, Milan (IT); Marco Mozzati, Milan (IT)

(73) Assignees: PIRELLI & C. S.P.A., Milan (IT); TELECOM ITALIA S.P.A., Milan (IT)

( * ) Notice: Subject to any disclaimer, the term of this patent is extended or adjusted under 35 U.S.C. 154(b) by 962 days.

(21) Appl. No.: 12/809,459

(22) PCT Filed: Dec. 21, 2007

(86) PCT No.: PCT/EP2007/011359
§ 371 (c)(1),
(2), (4) Date: Sep. 3, 2010

(87) PCT Pub. No.: WO2009/080082
PCT Pub. Date: Jul. 2, 2009

(65) Prior Publication Data
US 2011/0054337 A1  Mar. 3, 2011

(51) Int. Cl.
- *A61B 5/02* (2006.01)
- *A61B 5/00* (2006.01)
- *A61B 5/0432* (2006.01)

(52) U.S. Cl.
CPC ........... *A61B 5/0006* (2013.01); *A61B 5/04325* (2013.01)

(58) Field of Classification Search
CPC ............. A61N 1/37252; A61N 1/3727; A61B 5/0006; A61B 5/02; A61B 5/024; A61B 5/0245; A61B 5/0402; H04J 3/06; H04J 3/0635; H04J 3/0638; H04J 3/0652; H04J 3/0658; H04J 3/0685

USPC ............ 128/903; 600/523; 607/30, 31, 32, 60
See application file for complete search history.

(56) References Cited

U.S. PATENT DOCUMENTS

| | | |
|---|---|---|
| 6,589,170 B1 | 7/2003 | Flach et al. |
| 6,842,438 B1 | 1/2005 | Benedict et al. |

(Continued)

FOREIGN PATENT DOCUMENTS

| | | |
|---|---|---|
| DE | 197 31 986 A1 | 1/1999 |
| EP | 1 168 690 A2 | 1/2002 |

(Continued)

OTHER PUBLICATIONS

Roche, P. A. et al, "Using a Cell Phone for Biotelemetry," Proceedings of the 2005 IEEE 31$^{st}$ Annual Northeast Bioengineering Conference, pp. 65-66, (2005).

(Continued)

*Primary Examiner* — Christopher D Koharski
*Assistant Examiner* — Frances Oropeza
(74) *Attorney, Agent, or Firm* — Finnegan, Henderson, Farabow, Garrett & Dunner, L.L.P.

(57) ABSTRACT

A method of processing in a medical device an electric biological signal collected from a patient, includes: a) acquiring a plurality of samples from the electric biological signal according to a sampling process wherein each sample is taken from the electric biological signal and memorized; b) during the sampling process of a), monitoring an active/inactive status of a radio time-division-multiplexing transmission of signals from the medical device over a radio communication network; and, when the status of the radio time-division-multiplexing transmission becomes active, c) preventing in a) the acquisition of any of the plurality of samples, which according to the sampling process should be acquired during the active status of the radio time-division-multiplexing transmission, from being performed until the radio time-division-multiplexing transmission remains in the active status.

29 Claims, 7 Drawing Sheets

(56) References Cited

U.S. PATENT DOCUMENTS

| | | | |
|---|---|---|---|
| 6,897,788 B2 * | 5/2005 | Khair et al. | 340/870.16 |
| 6,978,181 B1 * | 12/2005 | Snell | 607/60 |
| 7,301,451 B2 * | 11/2007 | Hastings | 340/539.12 |
| 2001/0023315 A1 * | 9/2001 | Flach et al. | 600/300 |
| 2004/0133089 A1 | 7/2004 | Kilcoyne et al. | |
| 2004/0147969 A1 | 7/2004 | Mann et al. | |
| 2004/0158138 A1 | 8/2004 | Kilcoyne et al. | |
| 2004/0167580 A1 | 8/2004 | Mann et al. | |
| 2005/0043601 A1 | 2/2005 | Kilcoyne et al. | |
| 2005/0197680 A1 * | 9/2005 | DelMain et al. | 607/60 |
| 2006/0009810 A1 | 1/2006 | Mann et al. | |
| 2007/0232936 A1 | 10/2007 | Mann et al. | |

FOREIGN PATENT DOCUMENTS

| | | |
|---|---|---|
| EP | 1 589 464 A2 | 10/2005 |
| JP | 2002-219109 | 8/2002 |

OTHER PUBLICATIONS

International Search Report from the European Patent Office for International Application No. PCT/US2007/011359, mailed Sep. 16, 2008.

* cited by examiner

METHOD AND MEDICAL DEVICE FOR REDUCING THE EFFECTS OF INTERFERENCE GENERATED BY A RADIO TRANSMISSION FROM THE MEDICAL DEVICE

CROSS REFERENCE TO RELATED APPLICATION

This application is a national phase application based on PCT/EP2007/011359, filed Dec. 21, 2007.

BACKGROUND OF THE INVENTION

1. Field of the Invention

The present invention relates to the field of medical telemetry.

In particular, it relates to the field of medical telemetry wherein a medical device remotely collects an electric biological signal from a patient, processes the collected electric biological signal and transmits processed data to a centralized monitoring station over a radio communication network. From the centralized monitoring station, a technician or a doctor can monitor in real time the physiologic status of the patient.

For example, the electric biological signal may be an electric cardiac signal or an electric signal associated with activity of skeletal muscle.

The centralized monitoring station and/or the remote telemeter may support suitable diagnostic function for alerting the technician/doctor and/or the patient whenever a predetermined physiologic event occurs, such as a cardiac arrhythmia condition.

2. Description of the Related Art

US 2001/0023315 discloses a medical telemetry system for collecting real-time physiological data of patients of a medical facility, and of transferring the data via RF (Radio Frequency) to a real-time data distribution network for monitoring and display. The system includes battery-powered remote telemeters which attach to respective patients, and which collect and transmit (in data packet) the physiological data of the patients.

The remote telemeters communicate bi-directionally with a number of ceiling-mounted RF transceivers using a wireless TDMA (Time Division Multiple Access) protocol. The RF transceivers, which are hard-wire connected to a LAN, forward the data packets received from the telemeters to patient monitoring stations on the LAN.

JP 2002 219109 discloses a system wherein patient's ECG information is transmitted to an automatic diagnostic analyzer at a supervisory centre by cellular phone.

Paul A. Roche et al. ("Using a Cell Phone for Biotelemetry", proceedings of the 2005 IEEE 31$^{st}$ Annual Northeast Bioengineering Conference, p. 65-66) discuss the benefits, obstacles, and methods of using cell phones to transmit biological waveforms to increase the mobility of patient monitoring. The Authors state that shielding the input cables will reduce the differential RF interference. Moreover, they state that the immunity of the sensitive electronics can be increased by inserting low-pass filters with maximum insertion loss at the cell phone's transmission frequency, reducing the RF seen at the inputs.

EP 1 589 464 discloses a diagnostic device comprising different sensors which can collect different electric biological signals such as heart rate, arterial pressure etc.; an analog-to-digital converter; a portable signal receiver which can analyze and process digitally converted data; and a transmission module to activate tele-transmission, via a telephone modem or GSM, to a central server. This document states that the analog-to-digital converter is placed close to the sensors so that the signals can be converted immediately on reception and transmitted digitally which is easier to manage and significantly reduces external interference.

As to the techniques disclosed by the above mentioned Paul A. Roche et al. to reduce interference problems, the Applicant notes that cable shielding can be insufficient. In particular, cable shielding can be inadequate to reduce interference occurring at the cable junctions (e.g., in the proximity of electrodes and connectors).

Moreover, as to the low-pass filtering technique disclosed by Paul A. Roche et al., the Applicant notes that such technique can be not adequate when an analog to digital (A/D) conversion of the collected biological waveform has to be performed for further data processing. In fact, in these cases, according to Shannon theorem, the collected biological waveform will be typically sampled at a sampling frequency that is at least twice the biological frequency range (which is usually below 200 Hz). Moreover, in order to improve performances, the biological waveform will be typically oversampled at a sampling frequency that is at least three or four times the biological frequency range. Therefore, considering that medical devices with high accuracy and sensitivity may use a sampling frequency of 500 Hz, the cut-off frequency of the low-pass filter should be of at least 250 Hz. Therefore, a low-pass filter with cut-off frequency of not less of 250 Hz will be not adequate to filter out the GSM (Global System for Mobile communications) standard's demodulated frame rate of 217 Hz.

SUMMARY OF THE INVENTION

The Applicant started from the observation that, between the collected electric biological signals and the signals transmitted by the medical device through a radio communication network, interferences may occur at the cable conveying the collected electric biological signals from the electrodes in contact with the patient's body to the medical device and at the junction points of the cable. He has remarked that such interference may significantly disturb the electric biological signal acquisition to the extent that the electric biological signal may result undecipherable and a diagnostic algorithm inapplicable.

Accordingly, the Applicant faced the technical problem of effectively reducing the effects of interference in a medical device.

In particular, the Applicant faced the technical problem of providing a method of electric biological signal processing and a medical device that allow to significantly reduce the effects of the interference between a collected electric biological signal and a signal transmitted by the medical device through a radio communication network that uses a time-division-multiplexing transmission scheme.

The Applicant found that this problem can be solved by sampling the electric biological signal collected from the patient; keeping monitoring the status (active/inactive) of the radio time-division-multiplexing transmission used by the medical device to send signals over a radio communication network; and, during the sampling process, preventing acquisition of any electric biological signal sample, which according to the sampling process should be performed during an active status of the radio time-division-multiplexing transmission, from being performed till the radio time-division-multiplexing transmission remains active.

Accordingly, in a first aspect the present invention relates to a method of processing in a medical device an electric biological signal collected from a patient, the method comprising:

a) acquiring a plurality of samples from the electric biological signal according to a sampling process wherein each sample is taken from the electric biological signal and memorized;

b) during the sampling process of a), monitoring an active/inactive status of a radio time-division-multiplexing transmission of signals from the medical device over a radio communication network; and, when the status of said radio time-division-multiplexing transmission becomes active, c) preventing in a) the acquisition of any of the plurality of samples, which according to said sampling process should be acquired during said active status of the radio time-division-multiplexing-transmission, from being performed till the radio time-division-multiplexing transmission remains in said active status.

In the present description and claims the expression "sample acquisition" is used to indicate both the action of taking a sample from an analog electric biological signal and the action of memorizing the taken sample. Acquisition of a sample is prevented if at least one of the two actions is not performed. In particular, sample acquisition can be prevented if the sample is not taken and no value for the not taken sample is memorized, or if the sample is not taken but a predetermined value for the not taken sample is memorized, or if the sample is taken but not memorized as it is.

Advantageously, the sampling process in a) is a periodic sampling process having a sampling period $T1$. Within each interval of time $T1$, sample acquisition is advantageously performed for a predetermined active time slot $Ts1$, with $Ts1<T1$. Within each predetermined active time slot $Ts1$ at least one sample is advantageously acquired.

Advantageously, according to said radio time-division-multiplexing transmission, signal transmission is performed according to a transmission period $T2$. Moreover, within each interval of time $T2$, signal transmission is advantageously active for a predetermined active time slot $Ts2$, with $Ts2<T2$.

Advantageously, samples are acquired in a) at an acquisition rate $1/T1$ that is at least twice the frequency range of the collected electric biological signal. Advantageously, the acquisition rate $1/T1$ is higher than at least twice the frequency range of the collected electric biological signal.

Advantageously, when the status of said radio time-division-multiplexing transmission becomes inactive again, the sampling process of a) is resumed.

Advantageously, the monitoring in b) is continuously carried on during the execution of a).

Advantageously, when in b) the status of said radio time-division-multiplexing transmission is inactive the sampling process of a) is carried on.

According to a first embodiment, c) is performed by preventing any of the plurality of samples, which according to said sampling process should be acquired during the active status of the radio time-division-multiplexing transmission, from being taken and memorized till the radio time-division-multiplexing transmission remains in said active status.

In the first embodiment, b) is advantageously performed in parallel to a).

Typically, the electric biological signal is collected through n analog input channels, wherein n is an integer at least equal to 2. As known in the art, in case of ECG electric biological signal, n is typically equal to three or ten. Advantageously, within each active acquisition time slot $Ts1$, n samples are acquired (a sample of each of the n analog input channels is acquired).

In the case in which, in the first embodiment, n samples are acquired within each active acquisition time slot $Ts1$ and when in b) the status of said radio time-division-multiplexing transmission becomes active, the method advantageously further comprises d) checking if sample acquisition in a) is momentarily active (that is, if the sampling process in a) is within one of the predetermined active time slots $Ts1$).

Advantageously, c) is executed in the negative case of d). Preferably, c) is executed only in the negative case of d).

In the positive case of d), the execution of a) (and b)) is carried on.

Moreover, if—during the interval of time said radio time-division-multiplexing transmission has been active—sample acquisition has been prevented in c), the sampling process of a) is advantageously resumed with a predetermined delay $Tx$ lower than $T1$. Advantageously, the following condition is met: $0<Tx\leq Ts1$.

Moreover, in the first embodiment, within each active acquisition time slot $Ts1$ of the sampling process of a), after taking each of the n samples and before memorizing it, the method further comprises e) checking if said radio time-division-multiplexing transmission is in an active status. In the positive case of e), the value of the taken sample is corrected according to a predetermined correction procedure and the value of the corrected sample is memorized. In the negative case of e) the value of the taken sample is memorized as it is.

The correction in e) can be performed, for example, by setting the value of the taken sample to zero or by replacing the value of the taken sample with the value of the corresponding second-last acquired sample (that is, with the value of the sample memorized in the previous acquisition time slot $Ts1$ for the same channel).

According to a variant, in a), within each active acquisition time slot $Ts1$, before taking each of the n samples, the method further comprises e') checking if said radio time-division-multiplexing transmission is in an active status. In the positive case of e), the sample is not taken and a predetermined value is memorized for the not taken sample. For example, the value of the second-last acquired sample or, according to a variant, a null value is memorized for the not taken sample. In the negative case of e'), the sample is taken and memorized as it is.

According to a second embodiment, b) is performed by monitoring the active/inactive status of said radio time-division-multiplexing transmission after taking each of the plurality of samples in a). When the status of said radio time-division-multiplexing transmission becomes active, c) is performed by not memorizing the taken sample. Advantageously, the value of the taken sample is corrected according to a predetermined correction procedure. Then, the value of the corrected sample is advantageously memorized.

The correction can be performed, for example, by setting the value of the taken sample to zero or by replacing the value of the taken sample with the value of the second-last acquired sample (that is, with the value of the sample memorized in the previous acquisition time slot $Ts1$ for the same channel).

According to a third embodiment, b) is performed by monitoring the active/inactive status of said radio time-division-multiplexing transmission before taking each of the plurality of samples in a). When the status of said radio time-division-multiplexing transmission becomes active, c) is advantageously performed by not taking the sample. Advantageously, a predetermined value is memorized for the not acquired sample. For example, the value of the second-last acquired sample or, according to a variant, a null value is memorized for the not acquired sample.

Said radio time-division-multiplexing transmission advantageously is a time division multiple access transmission (TDMA).

Said radio time-division-multiplexing transmission is performed according to at least one cellular transmission standard selected from the group comprising: GSM, GPRS and EGPRS (Enhanced GPRS).

Said radio communication network can be a GSM, GSM/GPRS and/or GSM/EGPRS mobile network.

In a second aspect the present invention relates to a medical device comprising input modules for collecting an electric biological signal, processing modules connected to the input modules, and a transceiver section comprising a mobile data terminal connected to the processing modules, the transceiver section being adapted to be connected to a radio communication network and to transmit and receive signals by using a time-division-multiplexing transmission and the processing modules being adapted:

a) to acquire a plurality of samples from the collected electric biological signal according to a sampling process wherein each sample is taken from the collected electric biological signal and memorized;

b) during the sampling process of a), to monitor an active/inactive status of the radio time-division-multiplexing transmission of signals from the transceiver section; and, when the status of said radio time-division-multiplexing transmission becomes active, c) to prevent in a) the acquisition of any of the plurality of samples, which according to said sampling process should be acquired during said active status of the radio time-division-multiplexing transmission, from being performed till the radio time-division-multiplexing transmission remains in said active status.

As far as concerns further features of actions a) to c) reference is made to what already disclosed above with reference to the first aspect of the invention.

The transceiver section is advantageously adapted to transmit/receive signals according to GSM, GSM/GPRS and/or GSM/EGPRS cellular transmission standards.

The signals transmitted by the transceiver section can include text and/or multimedia messages, data concerning the acquired electric biological signal and GSM/GPRS/EGPRS signaling.

The transceiver section is advantageously adapted to transmit said signals through a Short Messaging System (SMS), a Multimedia Messaging System (MMS), and/or a suitable file transfer protocol (e.g., FTP).

Said mobile data terminal is advantageously also adapted to receive signals through SMS and, optionally, MMS.

Said mobile data terminal is also advantageously adapted to support signaling communications with the radio communication network to be enabled to access GSM, GSM/GPRS and/or GSM/EGPRS network services.

Advantageously, the mobile data terminal is adapted to provide the processing modules with data indicative of the status (active/inactive) of the radio time-division-multiplexing transmission. The processing modules are advantageously adapted to determine the status of the radio time-division-multiplexing transmission by reading said data.

Advantageously, the medical device further comprises a user interface.

Advantageously, the input modules are adapted to receive the electric biological signal from a cable that connects the input modules to electrodes to be positioned on the patient's body.

Typically, the input modules comprise n input channels (wherein n is an integer≥2) for receiving the electric biological signal collected by a corresponding number of electrodes.

Advantageously the medical device is a portable device.

According to an embodiment, the medical device is an electrocardiograph.

According to an embodiment, the medical device is an electromyograph.

BRIEF DESCRIPTION OF THE DRAWINGS

The features and advantages of the present invention will be made apparent by the following detailed description of some exemplary embodiments thereof, provided merely by way of non-limiting examples, description that will be conducted by making reference to the attached drawings, wherein.

DETAILED DESCRIPTION OF THE INVENTION

Figure 1:
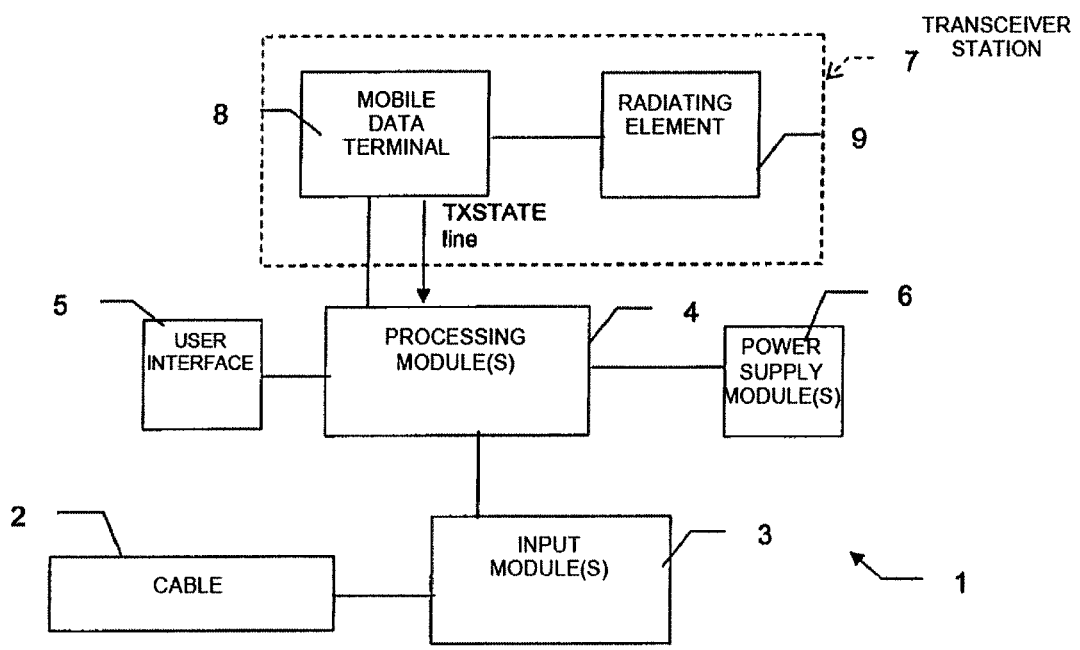
FIG. 1 schematically shows an embodiment of a medical device according to the invention.

FIG. 1 schematically shows a medical device 1 according to an exemplarily embodiment of the invention.

Advantageously the medical device 1 is a portable device.

The medical device 1 of FIG. 1 comprises a cable 2, input modules 3, processing modules 4, a user interface 5, power supply modules 6 and a transceiver section 7, comprising a mobile data terminal 8 and a radiating element 9.

The cable 2 comprises a number of wires (not shown), each wire being terminated at one end by an electrode (not shown) to be positioned in contact with a patient's body. Moreover, the cable 2 comprises a connector (not shown) for connection of the wires to the input modules 3, which receives the electric biological signals from a number of input channels (not shown).

For example, in case of ECG acquisition, the ECG cable 2 may conventionally comprise five surface electrodes: three to be positioned at the position of three standard ECG leads, one as reference electrode and one as ground electrode. The five electrodes can be positioned on the patient's chest and three wires can connect the three electrodes to be positioned at the position of three standard ECG leads to three input channels of the input modules 3.

The cable 2 is advantageously shielded according to techniques well known in the art to reduce external interference.

The input modules 3 are adapted to process, according to techniques well know in the art, the analog electric biological signals collected by the electrodes, including, for example, amplification and filtering. Advantageously, each input channel is associated with a low-pass filter. The cut-off frequency can be the same for all input channels and is for instance of 250 Hz.

The power supply modules 6 are adapted to manage power supply of medical device 1, according to techniques well known in the art.

Advantageously the medical device 1 is battery supplied.

The transceiver section 7 is adapted to establish radio communications with a remote processing unit (not shown), such as an application server, through a radio communication network, by using a time-division-multiplexing transmission scheme.

According to an embodiment of the invention, radio communications are established according to GSM or GSM/GPRS and/or GSM/EGPRS standards.

In this case, transceiver section 7 is advantageously adapted to access GSM, GSM/GPRS and/or GSM/EGPRS radio mobile network services, receive and send SMS/MMS messages, and send data files through a GPRS or EGPRS connection (e.g., according to a File Transfer Protocol or FTP).

For connection to the GSM/GPRS/EGPRS network, the mobile data terminal 8 is advantageously equipped with a Subscriber Identity Module (SIM) identified by a univocal client number, i.e., the IMSI (International Mobile Subscriber Identity), and a dialable number, i.e., the MSISDN according to the standards, at which the transmission module can be reached.

The radiating element 9 is connected to the mobile data terminal 8 and advantageously comprises a conventional antenna to receive/send radio signals within GSM/GPRS/EGPRS frequency bandwidths.

The cable connecting the radiating element 9 to the mobile data terminal 8 is advantageously shielded according to techniques well known in the art to reduce interference.

Signal transmission towards the remote processing unit may be operated either by the patient, by a suitable diagnostic algorithm (according to predetermined pathological criteria) or by the remote processing unit.

The user interface 5 will typically comprise a liquid crystal display and a keyboard so as to allow the patient to configure the medical device; to display medical data (e.g., ECG patterns); to display information about an anomalous event (e.g., cardiac arrhythmia condition); to inform that a data transmission has been requested by the remote processing unit; to display a SMS/MMS message received from the remote processing unit; to write a SMS/MMS message to be sent to the remote processing unit, to display the battery charge status; to display the status (active/inactive) of signal transmission by the transceiver section 7; to display the status (active/inactive) of electric biological signal acquisition; and similar.

The processing modules 4 are adapted to control the collection of the analog electric biological signals, to process the electric biological signals collected by the electrodes, to suitably memorize the processed data, to run suitable diagnostic algorithms, to operate the transceiver section 7, to operate the user interface 5, to suitably convert the processed electric biological signals into files to be transmitted (e.g., according to FTP protocol) to the remote processing unit, and similar.

In particular, the processing modules 4 are adapted to carry out an analog-to-digital (A/D) conversion of the analog electric biological signal collected by the electrodes.

Advantageously, said A/D conversion is carried out according to a sampling process having a sampling period $T1$ and an active sample acquisition time slot $Ts1$. In particular, the sampling process is periodically active for a time slot $Ts1$ and inactive for a time slot $T1-Ts1$.

In general, an active sample acquisition time slot refers to the time slot in which at least one sample is taken and memorized.

The sampling rate $1/T1$ is preferably higher than twice the electric biological signal bandwidth.

For example, in case of ECG acquisition, considering that the bandwidth of the cardiac signal is about 100 Hz, the sampling rate $1/T1$ is preferably higher than 200 Hz.

Figure 2:
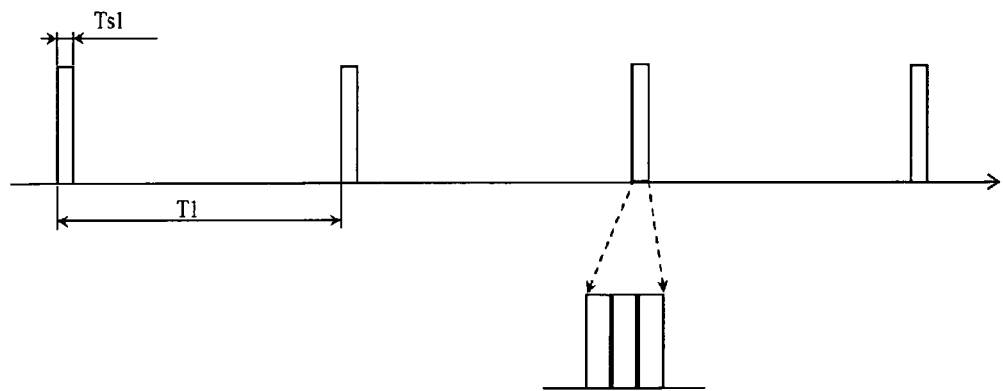
FIG. 2 schematically shows a time diagram of an ECG acquisition process.

FIG. 2 exemplarily shows a time diagram of a continuous sampling process with $T1=2$ ms (sampling rate of 500 Hz), $Ts1=18$ μs, and duty cycle ($Ts1/T1$) of 0.9%.

In the example of FIG. 2, a sample of each of three input channels (corresponding to three electrodes positioned on the patient at the position of three standard ECG leads) on the input modules 3 is acquired (taken and memorized), 6 μs each, within each time slot $Ts1$ of 18 μs.

After A/D conversion, the processing modules 4 are advantageously adapted to run suitable diagnostic algorithms to identify any anomalous condition and, if necessary, to command the transceiver section 7 to send suitable information (e.g., via SMS or file transfer) to the remote processing unit. For example, a SMS informing about the detected anomalous condition or a file containing the relevant ECG pattern may be sent to the remote processing unit.

Figure 3:
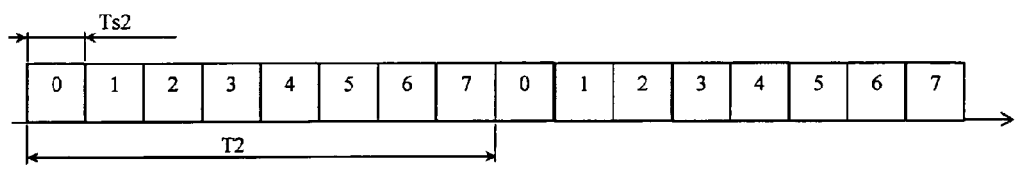
FIG. 3 schematically shows a time diagram of a TDMA transmission process according to GSM standard.

FIG. 3 exemplarily shows a time diagram of a TDMA transmission process according to GSM standard, having a frame rate of 217 Hz, a transmission period (the inverse of the frame rate) $T2$ of about 4.615 ms, an active transmission time slot $Ts2$ of about 577 μs, and a duty cycle ($Ts2/T2$) of 12.5%.

Figure 4:
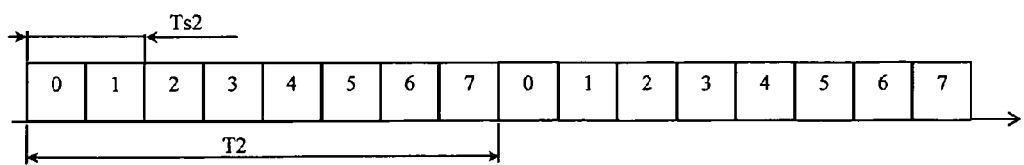
FIG. 4 schematically shows a time diagram of a TDMA transmission process according to GPRS and EGPRS standards.

In its turn, FIG. 4 exemplarily shows a time diagram of a TDMA transmission process according to GPRS and EGPRS standards, having a frame rate of 217 Hz, a transmission period (the inverse of the frame rate) $T2$ of about 4.615 ms, an active transmission time slot $Ts2$ of about 2*577 μs (twice the active transmission time slot of the GSM standard), and a duty cycle ($Ts2/T2$) of 25%.

In general, an active transmission time slot refers to the total time slot in which the transmission takes place and may comprise one or more transmission sub-units, e.g., of 577 μs each.

As well as for sending suitable information (via SMS or file transfer) to the remote processing unit, the mobile data terminal 8 may establish a radio TDMA communication to exchange service communications with the radio communication network. For example, service communications can be exchanged between the GSM/GPRS/EGPRS mobile data terminal 8 and the radio communication network, according to signaling procedures well known in the art, to enable the mobile data terminal 8 to be authenticated within the radio communication network, its position to be identified, and similar.

Any time a radio transmission from the transceiver section 7 of the medical device 1 is active, interference with the electric biological signal collected by the electrodes may occur. In particular, interference may occur during each active transmission time slot $Ts2$.

The present description refers in particular to the interference caused by the transmission of signals from the transceiver section 7 over the radio communication network. As to radio receptions by the transceiver 7, it is noted that the radio signals received by the transceiver section 7 from a GSM/GPRS/EGPRS base transmission station (BTS) are typically very low in power. Therefore, interference between the electric biological signal collected by the electrodes and any radio signals received by the transceiver section 7 typically does not lead to interference problems with the collected electric biological signal. Any way, if necessary, the principles of the present invention may also be applied to reduce the effects of the interference between the electric biological signal collected by the electrodes and any radio signals received by the transceiver section 7.

Typically, the medical device 1 does not support audio/video call, i.e., there is no exchange of speech or image signals over the radio link. In this way, the periods of possible interference between GSM/GPRS/EGPRS transmission and electric biological signal acquisition are limited to the above mentioned type of communications (SMS, file transfer and signaling).

Anyhow, GSM signals can be exchanged between the mobile data terminal 8 and the radio communication network during a call establishment procedure or ringing phase, regardless of the outcome of the procedure that in a mobile data terminal not supporting audio/video call would end with a rejection of a call.

The Applicant observed that signal transmission over the radio communication network is performed to comply with GSM/GPRS/EGPRS standards and can be operated any time, by request of the remote processing unit, such as an application server, the patient, the diagnosis algorithm or the radio communication network for service communications. Therefore, signal transmission over the radio communication network is out of the control of the processing modules 4, which perform sample acquisition of the analog electric biological signal.

Accordingly, in order to reduce the effects of the interference, the Applicant perceived the need of enabling the processing modules 4 to keep monitoring the status (active/inactive) of the radio transmission operated by the mobile data terminal 8 during the sampling process so that, when the radio transmission becomes active, the processing modules 4 are enabled to prevent acquisition of an electric biological signal sample, which according to the sampling process should start during the active status of the transmission, from being performed as long as the status of radio transmission remains active.

In order to allow monitoring of the radio transmission status, the mobile data terminal 8 advantageously provides a logic digital line (herein after called TXSTATE line) for signaling in real time the status of the radio transmission. For example, said logic line may take a logic value '0' to indicate that the radio transmission is inactive and a logic value '1' to indicate that the radio transmission is active.

The logic value of the TXSTATE line will be available at a pin of the mobile data terminal 8 that will be electrically connected to a corresponding input pin of the processing modules 4.

By monitoring the logic value taken by the TXSTATE line at said input pin, the processing modules 4 are thus given the possibility of real time identifying the radio transmission status.

Monitoring the status of the TXSTATE line is typically performed according to microprocessor interrupts procedures well known in the art.

Figure 5:
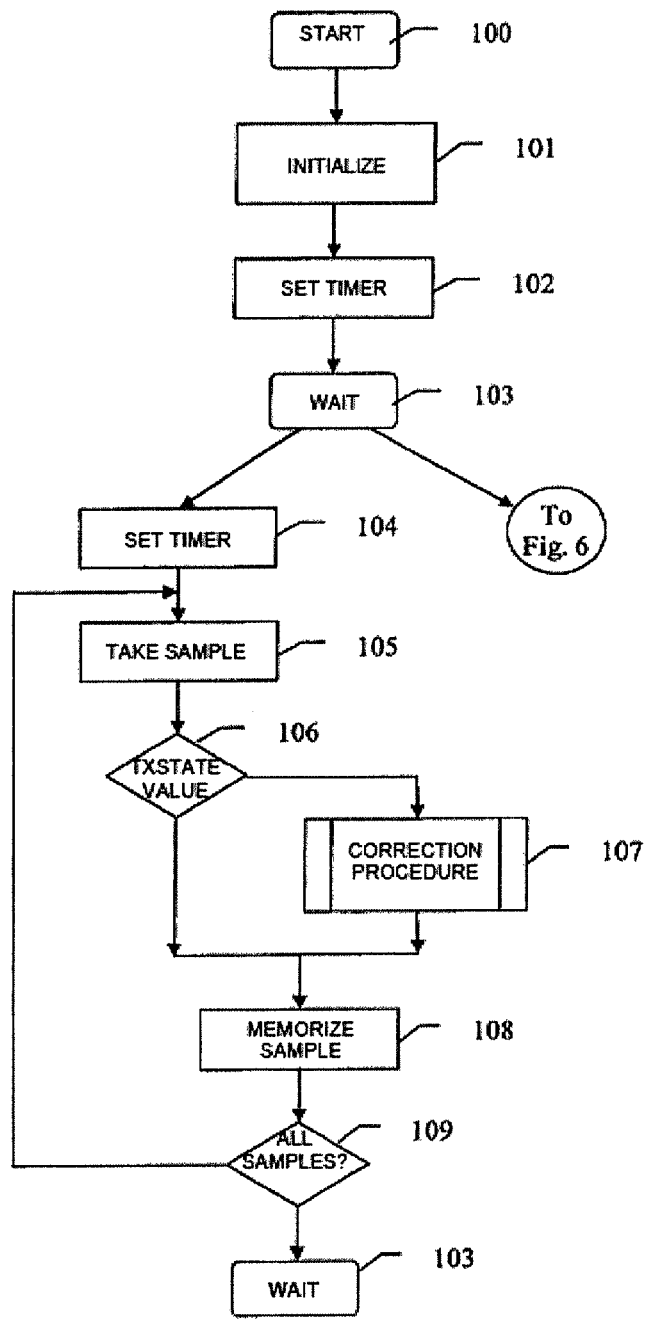
FIGS. 5 and 6 schematically show a flowchart outlining the main actions carried out to process an electric biological signal according to a first embodiment of the invention.
Figure 6:
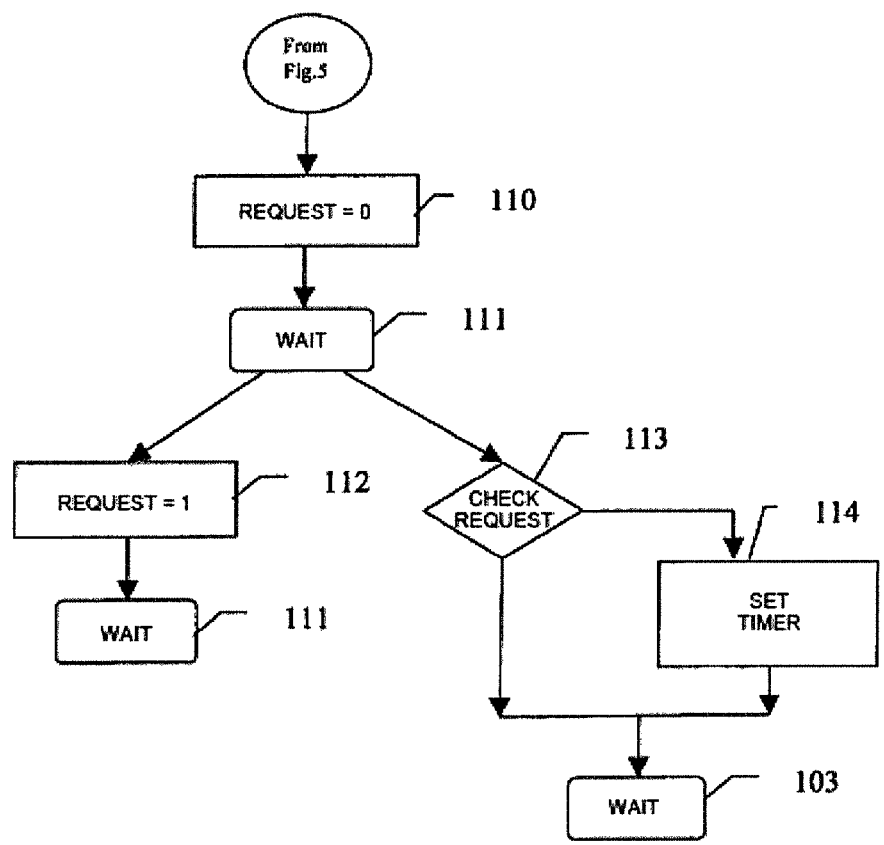

The flowchart shown in FIGS. 5 and 6 outlines the main actions carried out by the processing modules 4, according to a first preferred embodiment of the invention, to process the electric biological signal collected by the electrodes in order to reduce the effects of the interference.

In FIG. 5, at block 100 the processing modules 4 start the process, at block 101 they perform a initialization process (e.g., by clearing a processing modules memory) and at block 102 they set a timer for an interval of time T1.

At block 103 the processing modules 4 stay in a waiting state, waiting for one of two possible events: end of the interval of time for which the timer is set or change of TXSTATE line from the logic value '0' to '1'.

When the interval of time for which the timer is set ends, the timer is set again for an interval of time T1 (block 104) and a sample of each of the n input channels of the input modules 3 is acquired (blocks 105 to 109).

In particular, at block 105 a sample of one of the n input channels is taken.

At block 106 the logic value taken by the TXSTATE line is checked. If the logic value of the TXSTATE line is '0' (that is the radio transmission in momentarily inactive), the sample is memorized in the processing module memory (block 108). Then, at block 109, the processing modules 4 check if a sample of all n input channels has been acquired. In the affirmative, the processing modules 4 return in the waiting state of block 103. In the negative, the processing modules 4 loop back to block 105 to take a sample of another of the n input channels.

If, at block 106, the logic value taken by the TXSTATE line is '1' (that is the radio transmission in momentarily active), processing modules 4 carry out a correction procedure (block 107), before executing the memorizing action of block 108.

For example, according to an embodiment of the correction procedure, the processing modules 4 can replace the value of the last taken sample with the value of the corresponding second-last acquired sample (that is, with the value of the sample memorized in the previous acquisition time slot Ts1 for the same channel). According to another embodiment, they can replace the value of the last acquired sample with a null value.

It is noted that the latter embodiment simulates a situation of absence of electric biological signal that can be suitably handled by the diagnostic algorithm.

When, at block 103, the TXSTATE line value changes from the logic value '0' to '1', processing modules 4 set a variable REQUEST to zero (see block 110 of FIG. 6) and remain in a waiting state (block 111 of FIG. 6), waiting for one of two possible events: end of interval of time for which the timer is set or change of the TXSTATE line from the logic value '1' to '0'.

When the interval of time for which the timer is set ends, the processing modules 4 set the variable REQUEST to '1' (block 112) and return in the waiting state of block 111.

When the value of the TXSTATE line changes from the logic value '1' to '0' (that is, the radio transmission returns to be inactive), the processing modules check the value of the variable REQUEST (block 113). If the value of the variable REQUEST is '0' (that is, in the meantime the interval of time for which the timer was set did not elapsed yet), processing modules 4 return in the waiting state of block 103 of FIG. 5, wherein they wait for one of the two possible events: end of interval of time for which the timer is currently set (T1) or change of TXSTATE line from the logic value '0' to '1'.

If at the check of block 113 the value of the variable REQUEST is '1' (that is, in the meantime the interval of time for which the timer was set has elapsed), processing modules 4 set the timer for an interval of time Tx lower than T1 (block 114) before returning in the waiting state of block 103 of FIG. 5, wherein they wait for one of the two possible events: end of interval of time for which the timer is currently set (Tx) or change of TXSTATE line from the logic value '0' to '1'. This allows the sampling process performed at blocks 104 to 109 to be resumed with a delay Tx with respect to the end of the radio transmission (indicated by the passage of the TXSTATE line from the logic value '1' to '0' at block 113). For example, Tx meets the following condition: 0<Tx≤Ts1.

It is noted that in the flowchart of FIGS. 5 and 6 a not-ending sampling process is disclosed. However, the invention also contemplates the case wherein the sampling process is carried out for a predetermined period of time T3 (e.g., for few hours).

Moreover, it is noted that in the flowchart of FIG. 5, actions at blocks 103 to 109 allow the electric biological signal at n input channels of the input modules 3 to be periodically sampled with a sampling period T1. Actions at blocks 104 to 109 are started if the radio transmission is momentarily inactive (that is if the event "passage of the TXSTATE line from the logic value '0' to '1'" at block 103 has not occurred yet). During execution of the actions at blocks 104 to 109, a passage of the TXSTATE line from the logic value '0' to '1'" does not trigger itself any action. However, after taking each sample, the processing modules 4 check the status of the radio transmission (block 106 of FIG. 5). If in the meantime the radio transmission has become active (that is, if the TXSTATE line has passed from the logic value '0' to '1'"), the sample that has been just taken is corrected according to the correction procedure.

Actions at blocks 110 to 114 of FIG. 6 are carried out when the radio transmission becomes active (i.e., the TXSTATE line passes from the logic value '0' to '1') during an interval of time (T1-Ts1) in which the sampling process is inactive. According to these actions, a sample acquisition (including both the action of taking and memorizing the sample), which should start (according to the periodic sampling process) during an interval of time (Ts2) wherein the status of the transmission is active, is prevented from being performed till the radio transmission remains active.

Therefore, according to this first embodiment of the invention, the status of the radio transmission is monitored. When the radio transmission becomes active and the sampling process is momentarily inactive, the sampling process is prevented from becoming active as long as the radio transmission is active. This avoids samples to be acquired when there is a possibility of interference between the electric biological signal collected by the electrodes and the radio signals transmitted by the transceiver section 7.

Accordingly, this embodiment of the invention allows the chance of having an active radio transmission time slot (Ts2) to coincide with an active sample-acquisition time slot (Ts1) to be highly reduced.

Moreover, when the radio transmission becomes active during an interval of time (Ts1) in which the sampling process is momentarily active, the sample(s) taken during the interval of time (Ts2) in which the radio transmission is active (and, thus, when interference between the electric biological signal collected by the electrodes and the signals radio transmitted by the transceiver section 7 may have occurred) is (are) corrected before memorization.

Considering that the radio transmission is a TDMA transmission that, when operative, is periodically active only for a limited transmission time slot (Ts2), at most acquisition of a sample is postponed for an interval of time Ts2. By oversampling the electric biological signal (that is by using a sampling rate higher than twice the electric biological signal bandwidth as, for example, a sampling rate of 300, 400 or 500 Hz in case of cardiac signal), any degradation of the acquired electric biological signal due to postponement of sample acquisition can be kept acceptable.

Moreover, any degradation of the acquired electric biological signal due to postponement of sample acquisition or to sample correction is negligible with respect to the degradation that would be achieved in case of interference between the electric biological signal collected by the electrodes and the signals radio transmitted by the transceiver section 7.

Figure 7:
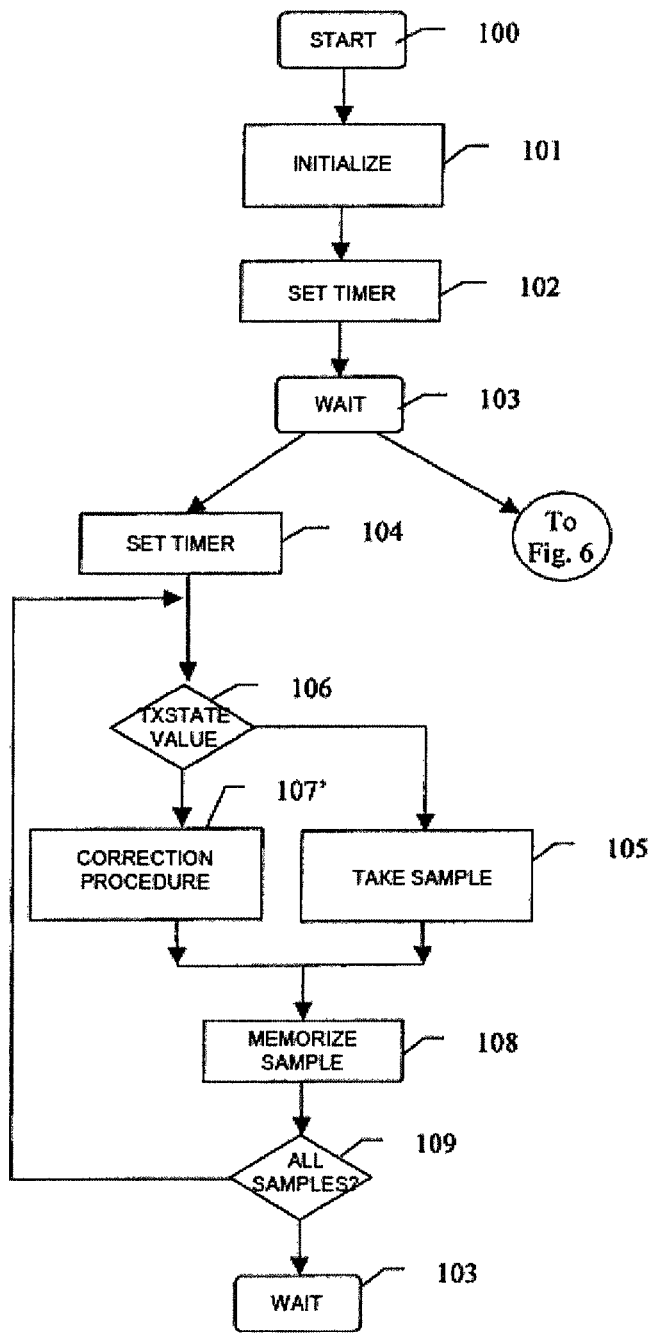
FIG. 7 schematically show a flowchart outlining the main actions carried out to process an electric biological signal according to a variant of the embodiment of FIGS. 5 and 6.

FIG. 7 shows a variant of the invention which is similar to that disclosed with reference to FIGS. 5 (and 6) apart from the fact that the check about the logic value taken by the TXSTATE line (block 106) is performed after action at block 104 and before action at block 105.

If, at block 106, the logic value of the TXSTATE line is '0' (that is the radio transmission in momentarily inactive), a sample of one of the n input channels is taken at block 105 and memorized in the processing module memory at block 108.

If, at block 106, the logic value taken by the TXSTATE line is '1' (that is the radio transmission in momentarily active), the sample is not taken and processing modules 4 set the value of the not taken sample to the value of the corresponding second-last acquired sample or, according to a variant, to a null value (block 107') and memorize such value in the processing module memory (block 108).

Figure 8:
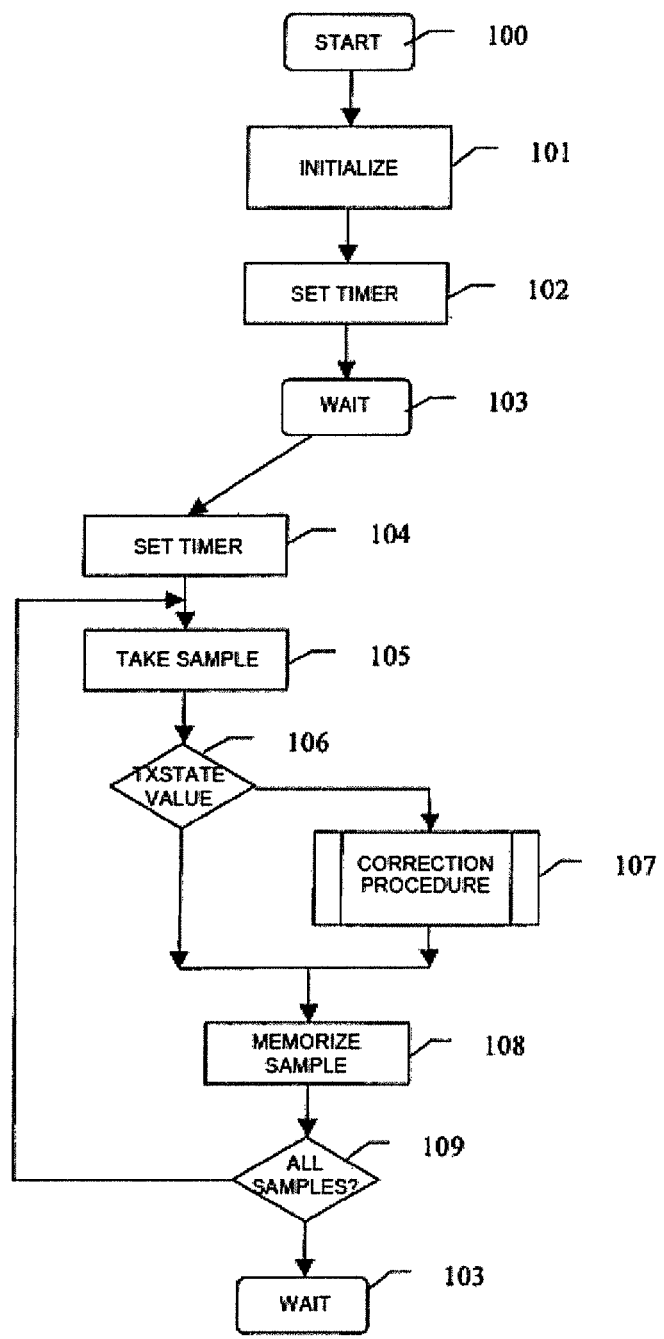
FIG. 8 schematically show a flowchart outlining the main actions carried out to process an electric biological signal according to a second embodiment of the invention.

FIG. 8 shows a second embodiment of the invention which is similar to that disclosed with reference to FIG. 5 apart from the fact that at block 103 the processing modules 4 stay in a waiting state, waiting for only one event: end of the interval of time for which the timer is set, and actions of the flowchart of FIG. 6 are not performed.

Figure 9:
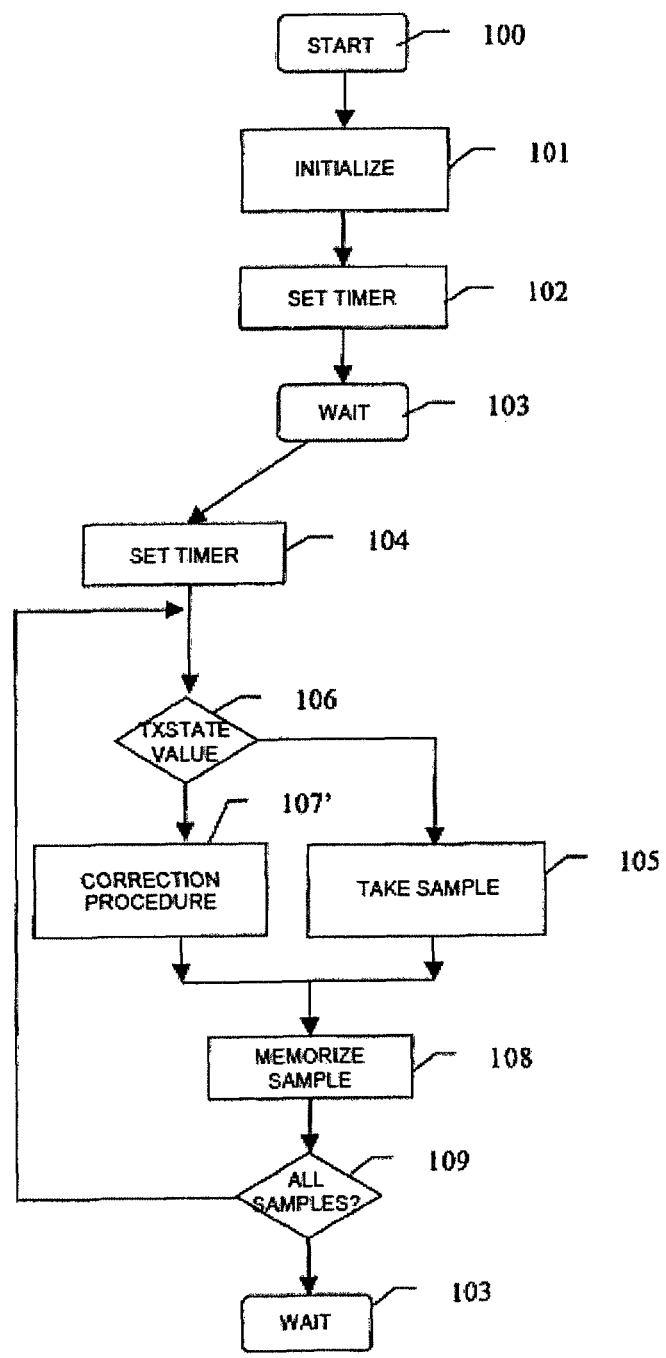
FIG. 9 schematically show a flowchart outlining the main actions carried out to process an electric biological signal according to a third embodiment of the invention.

FIG. 9 shows a third embodiment of the invention which is similar to that disclosed with reference to FIG. 7 apart from the fact that at block 103 the processing modules 4 stay in a waiting state, waiting for only one event: end of the interval of time for which the timer is set, and actions of the flowchart of FIG. 6 are not performed.

Accordingly, in the embodiment of FIG. 8, sample acquisition is prevented by not memorizing the value of the sample(s) taken when the radio time-division-multiplexing transmission is in an active status, correcting the value of such sample(s) and memorizing the value of the corrected sample(s).

In the third embodiment instead, sample acquisition is prevented by preventing the samples, which according to the sampling process should be acquired during an active status of the radio time-division-multiplexing transmission, from being taken and memorized till the radio time-division-multiplexing transmission remains in the active status, and by memorizing a predetermined value for the not acquired samples.

With respect to the second and third embodiment of FIGS. 8 and 9, the first embodiment of FIGS. 5, 6 and 7 is preferred in that—besides correcting the samples taken during the intervals of time the radio time-division-multiplexing transmission is in the active status or memorizing a predefined value for the samples not acquired during the intervals of time the radio time-division-multiplexing transmission is in the active status—it highly increase the chance of having the active radio transmission time slots (Ts2) and the active sample-acquisition time slots (Ts1) interleaved.

The invention claimed is:

1. A method of processing in a medical device an electric biological signal collected from a patient, comprising:
    a) collecting from a patient an analog electric biological signal;
    b) converting into digital the collected analog electric biological signal by sampling the collected analog electric biological signal, wherein a plurality of samples are taken from the collected analog electric biological signal and memorized;

c) during the sampling of the collected analog electric biological signal, monitoring when a radio time-division-multiplexing transmission of signals from the medical device over a radio communication network is active; and d) when the status of said radio time-division-multiplexing transmission becomes active, preventing the sampling of the collected analog electric biological signal from being performed as long as the radio time-division-multiplexing transmission remains in said active status.

2. The method according to claim 1, wherein the sampling of the collected analog electric biological signal is periodic with a sampling period T1.

3. The method according to claim 1, wherein within each period T1, sample acquisition is performed for a predetermined active time slot Ts1, with Ts1<T1.

4. The method according to claim 3, wherein at least one sample is acquired within each predetermined active time slot Ts1.

5. The method according to claim 4, wherein n samples are acquired within each active acquisition time slot Ts1, wherein n is higher than 1.

6. The method according to claim 1, wherein c) is performed by preventing any of the plurality of samples, which according to the sampling process should be acquired during the active status of the radio time-division-multiplexing transmission, from being taken and memorized until the radio time-division-multiplexing transmission remains in said active status.

7. The method according to claim 3, wherein, when the status of said radio time-division-multiplexing transmission becomes active, further comprising e) checking if the sampling of the collected analog electric biological signal is within one of the predetermined active time slots Ts1.

8. The method according to claim 7, wherein d) is executed in the negative case of e).

9. The method according to claim 8, wherein n samples are acquired within each active acquisition time slot Ts1, wherein n is higher than 1, and within each active acquisition time slot Ts1, after taking each of the n samples and before memorizing the n sample, further comprising a checking if said radio time-division-multiplexing transmission is in the active status.

10. The method according to claim 9, wherein, in the positive case of f), a value of the taken sample is corrected according to a predetermined correction procedure and the value of the corrected sample is memorized.

11. The method according to claim 8, wherein n samples are acquired within each active acquisition time slot Ts1, wherein n is higher than 1, and within each active acquisition time slot Ts1, before taking each of the n samples, further comprising e') checking if said radio time-division-multiplexing transmission is in an active status.

12. The method according to claim 10, wherein, in the positive case of e), the sample is not taken and a predetermined value is memorized for the not taken sample.

13. The method according to claim 1, wherein c) is performed after each sample of the plurality of samples is taken.

14. The method according to claim 13, wherein, when the status of said radio time-division-multiplexing transmission becomes active, d) is performed by not memorizing a taken sample.

15. The method according to claim 13, wherein, when the status of said radio time-division-multiplexing transmission becomes active, a value of the taken sample is corrected according to a predetermined correction procedure.

16. The method according to claim 15, wherein the value of the corrected sample is memorized after the predetermined correction procedure is complete.

17. The method according to claim 1, wherein b) is performed by monitoring the active/inactive status of said radio time-division-multiplexing transmission before taking each of the plurality of samples in a).

18. The method according to claim 17, wherein, when the status of said radio time-division-multiplexing transmission becomes active, c) is performed by not taking the sample.

19. The method according to claim 18, wherein a predetermined value is memorized for the not taken sample.

20. The method according to claim 1, wherein said radio time-division-multiplexing transmission is a time division multiple access transmission.

21. The method according to claim 20, wherein said radio time-division-multiplexing transmission is performed according to at least one cellular transmission standard selected from global system for mobile communications, GPRS and EGPRS.

22. A medical device comprising input modules for collecting an analog electric biological signal from a patient, processing modules connected to the input modules, and a transceiver section comprising a mobile data terminal connected to the processing modules, the transceiver section being configured to connect to a radio communication network and to transmit and receive signals by using a time-division-multiplexing transmission, and the processing modules being configured to:

a) carry out an analog-to-digital conversion of sample the collected analog electric biological signal by sampling the collected analog electric biological signal, wherein each sample is taken from the collected analog electric biological signal and memorized;

b) during the sampling of the collected analog electric biological signal, monitor when the radio time-division-multiplexing transmission of signals from the transceiver section is active; and c) when the status of said radio time-division-multiplexing transmission becomes active, prevent the sampling of the collected analog electric biological signal from being performed as long as the radio time-division-multiplexing transmission remains in said active status.

23. The medical device according to claim 22, wherein the transceiver section is configured to transmit and receive signals according to at least one cellular transmission standard selected from global system for mobile communications, GPRS and EGPRS.

24. The medical device according to claim 22, wherein the mobile data terminal is configured to provide the processing modules with data indicative of the status of the radio time-division-multiplexing transmission.

25. The medical device according to claim 21, wherein the medical device is an electrocardiograph.

26. The method according to claim 1, wherein the radio time-division-multiplexing is performed according to a transmission period T2, wherein, within each interval of time T2, signal transmission is active for an active time slot Ts2, with Ts2<T2.

27. The method according to claim 26, wherein c) and d) are carried out by monitoring when the radio time-division-multiplexing transmission is within the active time slot Ts2, and when the radio time-division-multiplexing transmission is within the active time slot Ts2, preventing the sampling of the collected analog electric biological signal from being performed as long as the radio time-division-multiplexing transmission remains in said active time slot Ts2.

28. A method of processing in a medical device an electric biological signal, comprising: collecting from a patient an analog electric biological signal;
  sampling the collected electric biological signal with a sampling period T1, wherein within each sampling period T1, the sampling is performed for a predetermined sampling active time slot Ts1, with Ts1<T1;
  during the collected sampling of the electric biological signal, monitoring when a radio time-division-multiplexing transmission of signals from the medical device over a radio communication network is in an active status, the time-division-multiplexing transmission being performed in the active status according to a predetermined transmission period T2, wherein, within each transmission period T2, signal transmission from the medical device is active for a transmission active time slot Ts2, with Ts2<T2;
  when the status of the radio time-division-multiplexing transmission becomes active, preventing the collected sampling of the electric biological signal from being performed in the sampling active time slot Ts1 that occurs in the transmission active time slot Ts2.

29. A medical device comprising:
  input modules for collecting an electric biological signal from a patient,
  processing modules connected to the input modules, and
  a transceiver section connected to the processing modules, the transceiver section being configured to connect to a radio communication network and to transmit signals by using a time-division-multiplexing transmission having a predetermined transmission period T2, wherein, within each transmission period T2, signal transmission from the transceiver section is active for a transmission active time slot Ts2, with Ts2<T2,
  wherein the processing modules are configured to:
    sample the collected electric biological signal with a sampling period T1, wherein within each sampling period T1, the sampling is performed for a predetermined sampling active time slot Ts1, with Ts1<T1;
    during the sampling of the electric biological signal, monitor when the radio time-division-multiplexing transmission of signals from the transceiver section is in an active status;
    when the status of the radio time-division-multiplexing transmission becomes active, prevent the sampling of the electric biological signal from being performed in the sampling active time slot Ts1 that occurs in the transmission active time slot Ts2.

* * * * *